US008885168B2

(12) United States Patent
Olesen (10) Patent No.: US 8,885,168 B2
(45) Date of Patent: Nov. 11, 2014

(54) WIND TURBINE INCLUDING OPTICAL SENSOR SYSTEM

(75) Inventor: Ib Svend Olesen, Randers (DK)

(73) Assignee: Vestas Wind Systems A/S, Aarhus N. (DK)

(*) Notice: Subject to any disclaimer, the term of this patent is extended or adjusted under 35 U.S.C. 154(b) by 0 days.

(21) Appl. No.: 14/111,069

(22) PCT Filed: Apr. 13, 2012

(86) PCT No.: PCT/DK2012/050128
§ 371 (c)(1),
(2), (4) Date: Nov. 9, 2013

(87) PCT Pub. No.: WO2012/139592
PCT Pub. Date: Oct. 18, 2012

(65) Prior Publication Data
US 2014/0054894 A1    Feb. 27, 2014

Related U.S. Application Data

(60) Provisional application No. 61/474,765, filed on Apr. 13, 2011.

(30) Foreign Application Priority Data

Apr. 13, 2011    (DK) ................................ 2011 70174

(51) Int. Cl.
*G01N 21/55*    (2014.01)
*F03D 11/00*    (2006.01)
*G01H 9/00*    (2006.01)
*F03D 7/00*    (2006.01)

(52) U.S. Cl.
CPC ............ *F03D 11/0091* (2013.01); *G01N 21/55* (2013.01); *G01H 9/00* (2013.01); *F05B 2260/80* (2013.01); *F05B 2270/804* (2013.01); *Y02B 10/30* (2013.01); *Y02E 10/722* (2013.01); *F03D 7/00* (2013.01)
USPC ....................................................... 356/445

(58) Field of Classification Search
CPC ........... G01P 5/26; G01P 5/001; G01P 13/02; G01P 13/025; G01P 13/0066; G01P 13/0073; G01P 21/025; G01W 1/00; G01W 1/02; G01W 1/08; G01W 1/16; G01W 1/10; F05B 2270/804; F05B 2260/80; F05B 2260/82
See application file for complete search history.

(56) References Cited

U.S. PATENT DOCUMENTS 8,045,159 B2 * 10/2011 Egloff et al. .................. 356/328
2004/0096150 A1 * 5/2004 Laudo ............................. 385/24
(Continued)

FOREIGN PATENT DOCUMENTS

GB          2052048 A      1/1981
GB          2461566 A      1/2010
(Continued)

OTHER PUBLICATIONS

Danish Search Report, PA 2011 70174, Jan. 9, 2012.
(Continued)

*Primary Examiner* — Michael P Stafira
(74) *Attorney, Agent, or Firm* — Patterson & Sheridan, LLP (57) ABSTRACT

A wind turbine includes an optical sensor system comprising one or more optical sensors comprising: a sensor membrane; a light source for illuminating a surface of the sensor membrane; an optical dispersive element arranged to disperse the light from the light source; and a light detector for receiving a portion of the dispersed light beam after reflection from the surface of the sensor membrane and dispersion of the light beam by the optical dispersive element. The wavelength of the light received at the light detector varies as a function of the displacement of the sensor membrane and the light detector operatively provides an output based on changes in the wavelength of the received light. The wind turbine is operable based on an input to a wind turbine control system received from the optical sensor system.

23 Claims, 5 Drawing Sheets

(56) References Cited

U.S. PATENT DOCUMENTS

2009/0245305 A1* 10/2009 Jensen et al. ............. 372/29.011
2013/0036813 A1*  2/2013 Rakoczy et al. ........... 73/170.03
2013/0078095 A1*  3/2013 Olesen ............................ 416/61
2013/0314694 A1* 11/2013 Tchoryk et al. .............. 356/28.5

FOREIGN PATENT DOCUMENTS

GB        2466433 A      6/2010
GB        2472437 A      2/2011

OTHER PUBLICATIONS

International Search Report, PCT/DK2012/050128, Mar. 11, 2013.
Z. Hameed et al: "Condition monitoring and fault detection of wind turbines and related algorithms: A review", Renewable and Sustainable Energy Reviews, vol. 13, No. 1, Jan. 1, 2009, pp. 1-39, XP055029113, ISSN: 1364-0321, DOI: 10.1016/j.rser.2007.05.008 the whole document.

* cited by examiner

WIND TURBINE INCLUDING OPTICAL SENSOR SYSTEM

The present invention relates to an optical sensor system for a wind turbine and to a wind turbine incorporating such a sensor system. The invention finds particular application in the detection of turbulence or in the monitoring of vibration of a wind turbine component.

BACKGROUND OF THE INVENTION

In order to optimise the extraction of energy from the wind, wind turbines are typically equipped with a number of sensor devices, which may provide feedback to the control systems of the turbine. For example, sensor devices are commonly used for monitoring environmental conditions at the wind turbine as well as for measuring parameters of the wind turbine components, such as strain. Using the data obtained from these sensor devices, the wind turbine may be operated accordingly, such as controlling the pitch of the blades. Also the yaw of the nacelle, can be adjusted in order to make the wind turbine as efficient as possible at generating energy.

Sensor devices are also commonly used to monitor the condition of the wind turbine components so that damage to the component, or deterioration in the condition of the component can be detected and the necessary maintenance carried out as early as possible. This helps to improve the lifetime of the components and prevents premature or complete failure of the wind turbine. In addition, since certain types of damage can adversely affect the operation of the wind turbine, effective maintenance of the wind turbine components ensures that the wind turbine can operate as efficiently as possible. Such sensor systems are particularly important for wind turbines located in remote areas, such a offshore, coastal or elevated areas, where the time and cost associated with maintenance are relatively high.

Due to the height of most wind turbines, damage from lightning strikes is a recurring operational problem. The use of lightning conductors provides one way of drawing the energy from a lightning strike safely away from the struck component, which as a result may suffer minimal or no damage. However, lightning conductors will not always adequately protect sensor equipment mounted on or in wind turbine components. Sensor systems incorporating metallic components such as wiring and circuits are particularly susceptible to damage from an electrical discharge.

Additionally, the operation of sensor systems in a wind turbine may be adversely affected by the magnetic and electrical fields associated with heavy electrical and mechanical machinery present, for example in the nacelle. As a result, the sensor systems are not able to work in an optimal way.

For these reasons, it is generally preferred to reduce the number of electronic components used in sensor systems and to use optical elements where possible.

One type of sensor which has proved to be sensitive to EMC disturbance from heavy machinery in a wind turbine, such as the generator, are electrical microphones which may be used in acoustic sensors to monitor the condition of wind turbine components based on the sound emissions. It has therefore been previously proposed to use 'optical' microphones for sensor applications in wind turbines. Optical microphones detect air movements using a membrane which transfers any oscillations to a beam of light rather than an electrical signal.

For example, it has been previously proposed to provide wind turbines with sensor systems incorporating one or more optical microphones for detecting turbulence in the air flow at the wind turbine. In one proposed system, turbulence sensors are used for the detection of the accumulation of unwanted matter, such as ice or dirt, on the surface of the wind turbine blades. In another proposed application, similar turbulence sensors are used as part of a control system that controls an aerodynamic parameter of a wind turbine blade, such as pitch angle, based on turbulence measurements. Optical microphones have also been proposed for use in place of electrical microphones for detecting vibrations as part of a Condition Monitoring System for monitoring the generator or other equipment within the nacelle.

The known optical microphones have not typically performed as well as traditional electrical microphones, in particular, due to sensitivity of the microphone to movements of the associated optical fibres, which causes false signals to be generated. This problem is particularly serious in moving or rotating structures, such as wind turbines. The performance of many optical microphones is also adversely affected by the fact that the optical sensor must be attached to the sensor membrane, for example in the case of a Fibre Bragg Grating sensor. The membrane therefore becomes heavier and is not free to respond accurately to air movements. In addition, in existing arrangements for optical microphones, the required light generation and detection apparatus is relatively expensive, so that it is not economically feasible to use such systems on a commercial scale.

It would therefore be desirable to provide a sensor system incorporating a novel optical microphone arrangement, which has an improved performance and which overcomes the problems associated with existing optical microphones. It would be particularly desirable if such a system could be formed from relatively robust and low cost components such that the system is more economically feasible for use in wind farms. It would further be desirable if such a system could be readily adapted for a variety of different sensor applications on a wind turbine.

According to the present invention there is provided a wind turbine including an optical sensor system comprising one or more optical sensors, each sensor comprising: a reflective sensor membrane; a light source for illuminating a surface of the sensor membrane; an optical dispersive element arranged to disperse the light beam from the light source; and a light detector for receiving a portion of the light beam after reflection from the surface of the sensor membrane and after dispersion of the light beam by the optical dispersive element. The wavelength of the light received at the light detector varies as a function of the displacement of the sensor membrane and the light detector operatively provides an output based on changes in the wavelength of the received light. The wind turbine further comprises a controller for receiving data from the sensor system and based on the received data controlling an operating parameter of the wind turbine.

The term 'operating parameter' refers to any parameter of the wind turbine which affects the operation of the wind turbine. The parameter to be controlled based on the data received from the optical sensor system will depend upon the function of the sensor system and examples will be described below. In certain embodiments, the operating parameter to be controlled may be an aerodynamic parameter of the wind turbine blade, such as pitch or rotor rpm. In other embodiments, the operating parameter to be controlled may be a parameter of the generator, such as load, power or rpm.

SUMMARY OF THE INVENTION

The optical sensor of the wind turbines of the present invention provides a novel type of optical microphone, which has a variety of potential applications in the monitoring of the wind turbine during operation, as described in more detail below.

The optical sensor used in the wind turbines of the present invention works by detecting changes in the wavelength of the light received at the light detector, which are indicative of the movement of the sensor membrane relative to the light detector and light source. In the dispersed beam produced by the optical dispersive element, the different wavelengths of light are spread out or split to produce a dispersed, 'fan' beam. Each wavelength of light will travel at a slightly different angle relative to the sensor membrane, after the light beam has been reflected from the surface of the sensor membrane. The wavelength of light that is received at the light detector will depend upon the position of the sensor membrane relative to the fixed positions of the light source and the light detector.

The displacement of the sensor membrane can be directly derived from the measured changes in wavelength, based on simple trigonometric methods, since the positions of the light source and the light detector, as well as the angular dispersion of the light beam by the prism will be known and will remain fixed. The pattern of displacement of the sensor membrane gives an indication of the air flow at the surface of the sensor membrane, in the same way as a conventional electrical microphone.

Advantageously, the arrangement of the present invention allows the reflected light to be detected without the need to attach any detection components directly to the sensor membrane, which allows the sensor membrane to move freely in response to air movements at the surface. As a result, the sensor membrane can respond more quickly to air movements and provide a more accurate indication of air flow at the surface. The arrangement of the sensor membrane therefore resembles more closely that of an electric microphone and can provide a similar high performance whilst providing the benefit of using optical components, rather than electrical components.

The sensor used in the present invention is highly sensitive and even small displacements of the membrane can be readily detected through monitoring the wavelength of the reflected light received at the light detector. As there are few moving parts, the sensor is resistant to extreme changes in temperature and the operation of the sensor will not be affected by changes in the conditions, such as temperature or humidity. Furthermore, since the sensor uses optical fibres where possible rather than metallic wiring or circuitry, the performance of the sensor will not be affected by the electrical or magnetic fields of heavy equipment in the vicinity of the sensor and the risk of damage due to lightning strikes is reduced.

The light source and the light detector of the sensor used in the present invention can advantageously be provided by relatively cheap and robust components that are relatively easy to install and operate. The present invention therefore provides a cost effective sensor which is suitable for use in wind turbines on a commercial scale.

The light source of the optical sensor used in the present invention emits a single light beam, which is split into different wavelengths by the optical dispersive element to produce a dispersed beam with each different wavelength or colour refracted at a different angle. The light source may comprise any suitable optoelectronic device, including for example a light-emitting diode, a photodiode or a laser. Preferably, the light source further comprises an optical fibre and the light output from the optoelectronic device is inputted into the optical fibre, which transmits the light and directs the light at the surface of the sensor membrane. Depending upon the required position of the sensor in the wind turbine, the optoelectronic components can be located remotely such that they are protected from lightning strikes.

The 'light' emitted by the light source may be visible light or may alternatively be a non-visible type of electromagnetic radiation, such as infrared. In a first preferred embodiment, the light source emits light at an average wavelength of around 1500 nm. In a second preferred embodiment, the light source emits light at an average wavelength of around 800 nm.

The wavelength range of the light beam emitted from the light source is preferably relatively narrow. For example, the wavelength range of the light beam is preferably less than 10 nm, more preferably around 5 nm. In one particularly preferred embodiment, the light source emits a beam with a wavelength range of 1500 nm to 1505 nm.

The optical dispersive element splits the light beam from the light source into its constituent wavelengths, wherein each wavelength is refracted by a different angle to disperse the light beam into a fan or cone shape. For example, in the case of a beam of white visible light, the optical dispersive element breaks up the light into its constituent spectral colours to produce a dispersed, rainbow beam. The optical dispersive element may take the form of one or more prisms, diffraction gratings or any other beam splitting optical components.

The optical dispersive element may be mounted at various positions along the path of the light beam between the light source and the light detector, such that the dispersion of the light beam occurs at a different time relative to the reflection of the beam. In all cases, however, the same measurement principles may be used to monitor changes in the wavelength of the light received at the light detector and from this to determine any movement of the sensor membrane.

In a first embodiment of the invention, the optical dispersive element is mounted in front of the light source, between the light source and the sensor membrane, such that the surface of the sensor membrane is illuminated with the dispersed beam. The dispersed light beam is sent in a spread out manner from the light source and will hit the surface of the sensor membrane in a distributed pattern. Each wavelength of light will therefore also be reflected back from the sensor membrane at a slightly different angle, so that the reflected light is also in the form of a dispersed, 'fan' beam. Any movement of the sensor membrane as a result of air flow or vibration will cause movement of the dispersed beam so that a different portion of the beam is directed at the light detector and a different wavelength of light is received. In the first embodiment of the invention, the optical dispersive element is preferably an optical prism.

In a second embodiment of the invention, the optical dispersive element is provided at the surface of the reflective sensor membrane such that the light beam from the light source is incident on the optical dispersive element. The light beam from the light source is thereby split by wavelength and dispersed as it is reflected from the surface of the sensor membrane. The resultant dispersed beam will take the same form as described above in relation to the first embodiment of the invention. Any movement of the sensor membrane will cause a corresponding movement of the optical dispersive element and therefore also movement of the dispersed beam so that a different portion of the beam and therefore a different wavelength is received at the light detector.

In the second embodiment, the optical dispersive element may take any suitable form which is capable of varying the angle at which the incident light beam is reflected, based on wavelength. Suitable optical dispersive elements for application onto the sensor membrane would be known to the skilled person and include, for example, a diffraction grating such as a ruled grating or a holographic grating, or a type of optical filter.

In one preferred example, the optical dispersive element is in the form of a filter having angular dependence, which means that the wavelength spectrum of the dispersed beam reflected back from the filter will vary depending on the angle of incidence of the light beam on the filter. As the sensor membrane moves relative to the light source, the angle of incidence of the light beam on the filter will vary, causing the wavelength spectrum of the reflected, dispersed beam to vary. By monitoring the change in the wavelength received at the light detector, it is then possible to monitor the change in the angle of incidence of the light beam and therefore the movement of the sensor membrane. Suitable thin film filters having angular dependence are available from Semrock, Inc.

In the second embodiment, the optical dispersive element may be incorporated at the surface of the sensor membrane in a number of ways, which would also be known to the skilled person. Preferably, the optical dispersive element is in the form of a coating or thin film that is applied to an area of the surface of the sensor membrane, for example, using techniques such as photo deposition or vapour deposition. Alternatively, the optical dispersive element may be integrated into the sensor membrane.

In embodiments according to the second aspect of the invention, the optical dispersive element preferably covers a defined area of the surface of the sensor membrane, which coincides with the area illuminated by the light beam from the light source. The defined area may be relatively small compared to the overall area of the sensor membrane surface, for example, the optical dispersive element may cover an area of less than 5 mm$^2$, or less than 3 mm$^2$ or in some cases less than 1 mm$^2$.

In a third embodiment of the invention, the optical dispersive element is provided between the sensor membrane and the light detector, such that the light beam is not dispersed until after it has been reflected from the surface of the sensor membrane. Any movement of the sensor membrane as a result of air flow or vibration will cause movement of the reflected beam so that the beam hits the optical dispersive element at a slightly different angle and the position of the dispersed beam produced by the optical dispersive element will shift slightly. As with the other two embodiments described above, a different portion of the dispersed beam will then be directed at the light detector. In the third embodiment of the invention, the optical dispersive element is preferably an optical prism.

The use of optical dispersive elements to disperse a light beam from a light source is well known and the skilled person would be familiar with the available types of optical dispersive elements and the way in which they affect a light beam. Some background information regarding optical dispersive elements may be found, for example, in "*Application of surface-relief diffractive optics to helmet-mounted displays*" by C. Cotton, D. Faklis, J. Bowen and G. Morris, Storming Media (1991);

"*RITMOS: a micromirror-based multi-object spectrometer*" by R. Meyer, K. Kearney, Z. Ninkov, C. Cotton, P. Hammond and B. Statt, Proc. SPIE, 5492 (2004); and "*Interference filters and special filters*" published by Schott A G.

The light detector of the sensor used in the present invention is arranged to receive a portion of the light beam that is reflected from the surface of the sensor membrane and that has been dispersed at a certain position by the optical dispersion element. The range of wavelengths or angle of dispersed light received by the light detector must necessarily be less than the total wavelength range or angle of the reflected beam, to allow changes in the wavelength of the received light to be detected. The light detector is positioned so that the portion of the beam that is received will vary according to the position of the sensor membrane relative to the light detector. Suitable types of light detectors would be known to the skilled person. Preferably, the light detector comprises one or more optical fibres and a portion of the reflected light is received into the end of an optical fibre directed at the surface of the sensor membrane.

In one particularly preferred embodiment, the light detector comprises a WDM (wavelength division multiplexing) system in which a portion of the dispersed beam is received in a single optical fibre and directed as a single input to a demultiplexer, which splits the beam again into two or more separate outputs of different wavelengths. Each output is sent to a PIN diode and the two or more PIN diodes are connected to a differential amplifier.

As the sensor membrane moves relative to the light detector, the wavelength of light received at the light detector will vary in a continuous manner and the amplitude of one of the output wavelengths will increase whilst the other(s) decrease. By comparing the amplitudes of the different output signals, it is therefore possible to analyse the changes in wavelength of the received light and calculate the corresponding movement of the sensor membrane.

This type of light detector arrangement is particularly advantageous, since unlike with many conventional types of optical microphone, the output is relatively insensitive to movement in the optical fibres, for example, as a result of movement of the wind turbine components. This is because any movement will affect each of the wavelength outputs in the same way so that common changes will be cancelled out by the differential amplifier and will not cause great inaccuracies.

The light detector of sensors used in the present invention operatively provides an output based on changes in the wavelength of the received light. The output is preferably received at a processor, which processes the measured wavelength data to determine the pattern of displacement of the sensor membrane. Based on the information about the displacement of the sensor membrane, the processor can determine one or more parameters of the air flow, or vibration causing the displacement of the sensor membrane. The data processing carried out by the processor will depend upon the function of the sensor. In certain embodiments, the sensors will incorporate a processor, for example, as part of the light detector. In other embodiments, the processor will not form a part of the sensor itself but will be connected to the light detector in a sensor system.

The output from the light detector or the processor is received at a controller of the wind turbine, which controls an operating parameter based on the detected output. This may be the control of a parameter of a wind turbine component, in order to maximise the efficiency of the wind turbine. Alternatively, under certain circumstances for example upon detection of ice or damage to a component, the controller may cause the wind turbine to shut down and temporarily stop operating so that the problem can be resolved.

The sensor membrane of sensors used in the invention is arranged so that it is susceptible to the changes in air flow that are to be detected by the sensor. The membrane will typically be relatively thin, preferably between 0.5 mm and 2.0 mm, and is tensioned so that the likely air flow at the surface of the sensor membrane will result in only a small movement of the membrane surface. In practice, a range of movement of the membrane of the order of several micrometers has been found advantageous, although the necessary range of movement will depend upon the application.

The choice of material of the membrane will also depend upon the required application of the sensor but is critical to ensure that the membrane is suitable for measurement. A material that is too light and flexible will in many cases be too sensitive to air flow and will not be suitable for distinguishing between normal and abnormal air flow conditions. Preferably, the material is therefore sufficiently strong and stiff to ensure that only relatively strong vibrations (in the range of 10 to 100 Hz) are detected. Additionally, the sensor membrane must be formed of a material that has a sufficiently smooth, reflective surface to enable the light beam to be reflected effectively such that it can readily be detected by the light detector. Preferably, the sensor membrane is formed of a reflective polymeric material.

In certain embodiments, it may be possible to use a surface of a wind turbine component as the sensor membrane for the sensor of the present invention. For example, the outer surface of a wind turbine blade may provide a suitable sensor membrane for certain applications where it is desired to measure air flow at the surface of the blade.

In certain embodiments of the present invention, the light source and the light detector of the optical sensor system are operatively provided in a sensor cavity within a wind turbine blade component, such as a wind turbine blade, and the sensor membrane covers at least part of the cavity. The sensor cavity may be sealed. This allows the cavity environment to be maintained at levels of humidity and temperature that ensure good operation of the sensor membrane. Sealing the cavity also acts to keep the internal surface of the membrane clean so that the reflection of the light from the surface remains consistent. Furthermore, with the sealed cavity, the movement of the sensor membrane can be considered wholly attributable to variations in the air flow at the outer surface of the membrane so that the sensor can accurately monitor conditions. In certain cases, the cavity may be filled with a gas other than air, such as an inert gas, e.g. nitrogen.

The present invention also provides a wind turbine comprising an optical sensor system comprising: a plurality of optical sensors, as described above, and a processor for receiving the output from the light detectors of the one or more optical sensors and determining from the output the displacement of the sensor membrane, as also described above. Systems used in the present invention may include a single optical sensor, but more preferably include a plurality of optical sensors. This allows monitoring of the air flow or vibrations at several different locations on a wind turbine component, providing information for use in a more sophisticated sensor system.

Preferably, sensor systems used in the present invention further comprise a memory for recording the outputs from the light detectors of the one or more sensors over a predetermined time period, wherein the processor analyses the recorded outputs in order to determine a condition of the wind turbine over the time period. The 'condition' may be a condition of the component itself, such as accumulation of ice or dirt, or may be a condition of the environmental conditions at the component, such as the air flow. Specific examples of the potential uses of the memory are described below in relation to the different aspects of the invention.

Sensor systems used in the present invention may further comprise an electrically insulated housing containing at least the light source and the light detector. This allows the components of the sensor system that are vulnerable to electrical discharge, for example from lightning or stray currents in the electrical machinery, to be protected. The optical, non-metallic and mechanical elements of the sensor system can then be deployed in locations of the wind turbine that are susceptible to electrical discharge, such as on the exterior of the wind turbine, in particular on the wind turbine blades, or in the nacelle near to the electrical components such as the generator.

The sensor system described has a number of potential applications in wind turbines according to the invention. In a first aspect of the invention, the sensor system is adapted for use in monitoring the airflow at a surface of a wind turbine component, wherein the sensor membrane is operatively mounted at a surface of a wind turbine component for monitoring air flow across the surface and wherein the processor determines from the output of the light detector the type of airflow across the sensor membrane. In particular, the sensor systems of wind turbines according to the first aspect of the invention may be adapted for operatively detecting turbulent air flow at the surface of a wind turbine component, wherein the processor analyses variations in the wavelength of the received light at the light detector over a predetermined period of time to determine whether the air flow over the sensor membrane is turbulent.

Sensor systems of wind turbines according to the first aspect of the invention find particular application in the monitoring of airflow conditions at the surface of a wind turbine blade and in the detection of turbulent airflow across the blade surface.

In certain embodiments, the airflow at the blade surface can be monitored in order to indirectly monitor the surface condition of the blade. Changes in the blade condition, such as deterioration of the blade surface, for example due to erosion or corrosion, or accumulation of matter such as dirt or ice, will greatly affect the flow of air across the blade surface. Accumulation of dirt, for example, may manifest itself as a gradual increase in the turbulence detected at the surface. Ice accumulation may have the same effect in increasing the turbulence but the effect will be seen more quickly over a number of hours. The nature of the matter accumulating on the blade may therefore also be deducible from the output of the sensors. Preferably, such systems for monitoring the condition of the blade surface include a plurality of optical sensors on the windward and leeward side of the blade, so that a complete sensor view is obtained.

Similar sensor systems are preferably incorporated on each of the blades of a wind turbine. If desired, the different systems from the blades may be connected to a common processor. This enables the processor to compare the output from the different optical sensors of one blade with those of another. The processor can then give an indication of whether the blades are mounted and operating correctly, and can compare the condition of the different blades.

Preferably, in sensor systems of wind turbines according to the first aspect of the invention for monitoring the condition of the blade surface, the optical sensors are each provided in a sensor housing having walls that define a cavity, in which the light source and light detector are contained. The sensor is then mounted in the blade such that the sensor membrane separates the cavity from the outside air, and such that the membrane is in contact with the airflow across the surface of the blade.

Preferably, the sensor membrane and the blade surface are arranged so that they form a smoothly continuous blade surface. This ensures that the presence of the sensor membrane does not impact the aerodynamic properties of the blade and also prevents the introduction of obstructions at the blade surface which may affect the air flow patterns. If desired, the membrane may be painted the same colour as the surrounding component surface to ensure that the visual appearance of the wind turbine is not impaired.

Under some operating conditions, the airflow across the surface of the blade will be laminar, resulting in little or no disturbance of the sensor membrane. Turbulent air flow caused, for example, by stall or the accumulation of matter at the blade surface, will result in sudden and unpredictable movement of the membrane and associated changes in the wavelength of the light reflected back to the light detector.

The processor may take continuous or periodic readings from each of the plurality of optical sensors which may be recorded in the memory to develop a time log of changes in the airflow over the blade. The processor may determine a condition of the blade surface based on a change in the sensor outputs compared with past outputs. This allows past outputs to act as a reference for comparison with the instantaneous or current readings being taken. This comparative information may be used to determine large scale changes in the airflow that are indicative of problems with the component. Alternatively or in addition, the information from the optical sensors may be used to monitor the performance of a wind turbine blade to enable the continuing improvement and development of aerodynamic properties of wind turbine blades, such as blade shape.

In a second aspect of the invention, the sensor system is adapted for use in a blade control system. The blade control system comprises a sensor system as described above in relation to the first aspect of the invention for detecting turbulence at the surface of the blade, and a controller for receiving data from the processor of the sensor system and based on the detection of the state of the airflow controlling an aerodynamic parameter of the rotor blade.

Systems of wind turbines according to the second aspect of the invention allow the aerodynamic interaction of the blade with the air flow to be monitored in real time, and for the blade to be adjusted as desired based on a measure of turbulence.

In certain preferred embodiments of wind turbines according to the second aspect of the invention, the aerodynamic parameter for control is the pitch angle of the wind turbine blade. The controller preferably controls the pitch of the blades to minimise the turbulence at the blade surface and maximise the output power from the wind turbine. This offers a responsive and finely tuned rotor blade pitch control mechanism based on the immediate aerodynamic conditions of the wind turbine blade.

As described above in relation to the first aspect of the invention, under normal operating conditions of the wind turbine, the airflow across the blade surface will be laminar, resulting in little or not disturbance of the sensor membrane. Turbulent airflow caused by the pitch of the blade inducing stall-like conditions will result in sudden and unpredictable movement of the membrane and associated changes in the wavelength of the detected light.

To detect stall-like conditions, where the pitch angle of the blade is too large, the optical sensors are preferably located in greater numbers on the suction surface of the blade and more preferably in greater numbers towards the trailing edge of the suction side of the blade, than in other areas.

In alternative embodiments, the aerodynamic parameter for control is the blade shape, or the airflow past the blade. Provision of suitable mechanisms to dynamically change the blade shape or adjust the airflow past the blade can then be operated based on the detected conditions to ensure that operating conditions are maintained according to pre-set desired values or ranges, where possible. Known techniques for dynamically adjusting the shape of the blade include, for example, hinged flaps, microtabs, surface slots or slats, concave or convex surface bumps, and fluid filled cavities or voids inside the blade.

In a third aspect of the invention, the sensor system is adapted to function as a vibration sensor system for monitoring the vibration level of wind turbine components in order to detect abnormal operating conditions. For example, in certain preferred embodiments, the sensor system may be adapted to replace the accelerometers presently used to monitor the health of components within the nacelle, such as the generator, by monitoring the vibrations on the surface of the components. In the case of a generator, when a fault is developing or has developed, the generator has been found to have a different frequency of vibration to the frequency during normal operation. By detecting and analysing the vibration at the surface of the generator, problems that will impair the operation can be identified in advance of a breakdown occurring.

The sensor system is particularly suitable for application in a condition monitoring system for components of the wind turbine within the nacelle, such as the generator or gear box, since the system is formed of mostly optical elements which are not affected by the electrical or magnetic fields produced by the heavy machinery within the nacelle.

In other embodiments, a vibration sensor system as used in wind turbines according to the third aspect of the present invention may be used to monitor the vibration levels in a wind turbine component, such as a wind turbine blade or tower, due to wind loading during operation. Excessive levels of vibration can reduce the lifetime of wind turbine components and in some cases, cause damage to the components. It is therefore important to monitor the vibration levels so that the operating parameters of the wind turbine can be controlled in response to the detection of vibration levels above a threshold value. For example, the pitch angle of the wind turbine blades may be controlled in order to reduce vibration, or the wind turbine may be temporarily turned off. In addition, the vibration sensor system may be used to detect changes in the resonant frequency of the wind turbine blade, which would give an indication that the blade has been damaged, or is covered with ice or other matter.

In a fourth aspect of the invention, related to the third aspect described above, the sensor system is used as a microphone for monitoring the sound emitted from wind turbine components in order to detect abnormal operating conditions. For example, in certain preferred embodiments, the sensor system may be adapted to replace the microphones presently used to monitor the health of components within the nacelle, such as the generator, by monitoring the sound or acoustic waves emitted from the components. In the case of a generator, when a fault is developing or has developed, the generator has been found to emit a different sound to the sound emitted during normal operation. In a simple case, a particular sound may indicate that a bearing is damaged. By detecting and analysing the sound spectrum of the generator, problems that will impair the operation can be identified in advance of a breakdown occurring.

In a similar way, the sensor system may be used as a microphone to monitor noise or sound from other wind turbine components, including for example the gear box, a bearing such as a main bearing or a blade bearing, a gear such as a yaw gear, or a blade. The sensor system may be adapted according to the frequency of the sound which is to be monitored, for example, through selection of the type of material used to form the sensor membrane, the tension of the sensor membrane and/or the type of optical dispersive element.

The frequency and/or amplitude of the sound generated by the wind turbine component can be monitored directly through the monitoring of the frequency and amplitude of the movement of the sensor membrane in the sensor system. For any particular component, the frequency or amplitude associated with a certain type of damage or failure will be known and any change of the frequency or amplitude of the sound generated by the component from the normal levels towards the levels indicative of damage can be immediately identified. The necessary action to avoid or reduce further damage or to replace or repair the component can then be taken.

In the third and fourth aspects of the invention, the use of a sensor system comprising a type of optical microphone, without electronic components, is particularly advantageous since the sensor system is not sensitive to EMC disturbance. Furthermore, since the sensor system does not require the use of electrically conductive components, it can be safely installed in a wind turbine blade without increasing the risk of damage to the blade by lightning strikes.

Wind turbines according to the invention may comprise one or more sensor systems, as described above. Different sensor systems may be used to monitor different wind turbine components and/or different conditions.

In one preferred embodiment of a wind turbine according to the invention, a sensor system is operatively mounted on each wind turbine blade such that the sensor membrane is integral to the surface of the blade. Such a system can be adapted to monitor turbulence or vibration, as described above.

The present invention further provides an optical sensor system comprising one or more sensors, each sensor comprising: a reflective sensor membrane; a light source for illuminating a surface of the sensor membrane; an optical dispersive element arranged to disperse the light beam from the light source to produce a dispersed light beam; and a light detector for receiving a portion of the light beam after reflection of the light beam from the surface of the sensor membrane and after dispersion of the light beam by the optical dispersive element, wherein the wavelength of the light received at the light detector varies as a function of the displacement of the sensor membrane and wherein the light detector operatively provides an output based on changes in the wavelength of the received light. As described above, the optical dispersive element may be positioned between the light source and the sensor membrane, on the sensor membrane itself, or between the sensor membrane and the light detector.

The invention will now be further described by way of example only and with reference to the accompanying figures in which:

DETAILED DESCRIPTION OF THE INVENTION

Figure 1:
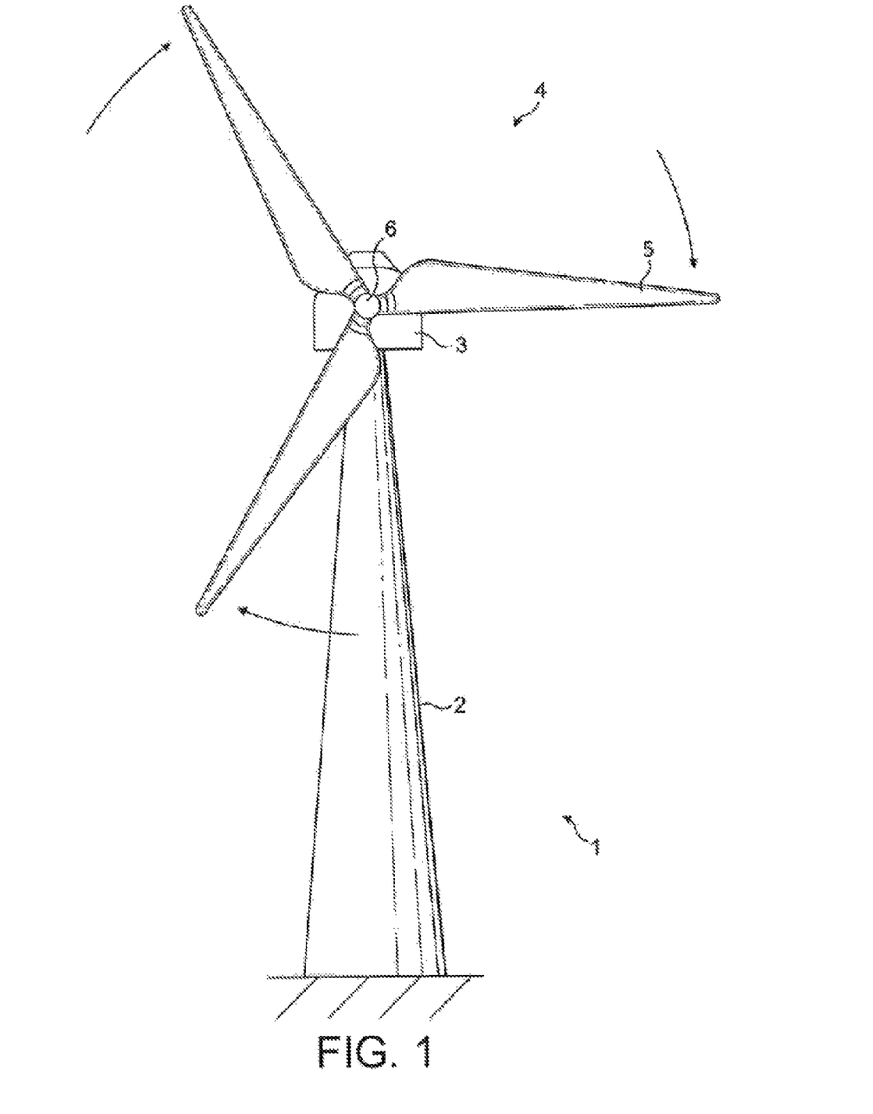
FIG. 1 illustrates a wind turbine.

FIG. 1 illustrates a wind turbine 1 according to the invention comprising a wind turbine tower 2 on which a wind turbine nacelle 3 is mounted. A wind turbine rotor 4 comprising three wind turbine blades 5 is mounted on a hub 6. The hub 6 is connected to the nacelle 3 through a low speed shaft (not shown) extending from the nacelle front. The wind turbine of FIG. 1 may be a small model intended for domestic or light utility usage, or may be a large model such as those that are suitable for use in large scale electricity generation on a wind farm. In the latter case, the diameter of the rotor may be as large as 100 meters or more.

Figure 2:
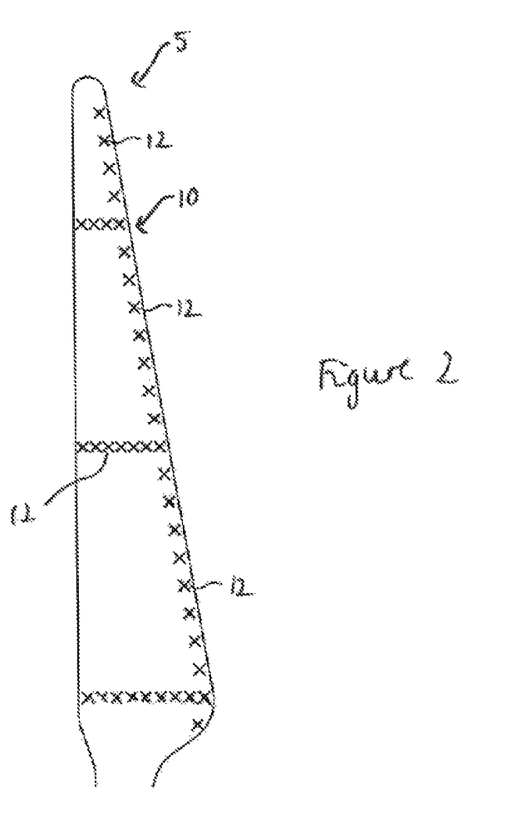
FIG. 2 is a longitudinal elevation of a wind turbine blade of the turbine of FIG. 1, showing an example arrangement of optical sensors in a turbulence sensor system.

Each wind turbine blade 5 incorporates a sensor system 10 comprising a plurality of turbulence sensors 12 spaced apart along the blade, as illustrated in FIG. 2 which shows a view of the leeward side of the blade 5. Turbulence sensors 12, as described in more detail below, are disposed along the surface of the blade 5 at a plurality of locations. Although it is possible in some embodiments that the sensors will be provided at equally spaced locations across the blade surface, in practice it is sufficient if they are disposed to give at least some coverage in the longitudinal and lateral directions of the blade. In the example shown in FIG. 2, the sensors are provided in a linear array disposed along the length of the blade and in a number of lateral, linear arrays spaced apart along the length of the blade and extending across the blade such that sensors are provided on both the windward and leeward sides.

In FIG. 2 the sensors are shown as being generally equally spaced, as this will allow data about the flow of air around the entire blade surface to be collected. It will however be appreciated that for detecting stall-like conditions, the area of most interest is the leeward trailing side of the blade and more sensors may therefore be mounted in that region.

Figure 3:
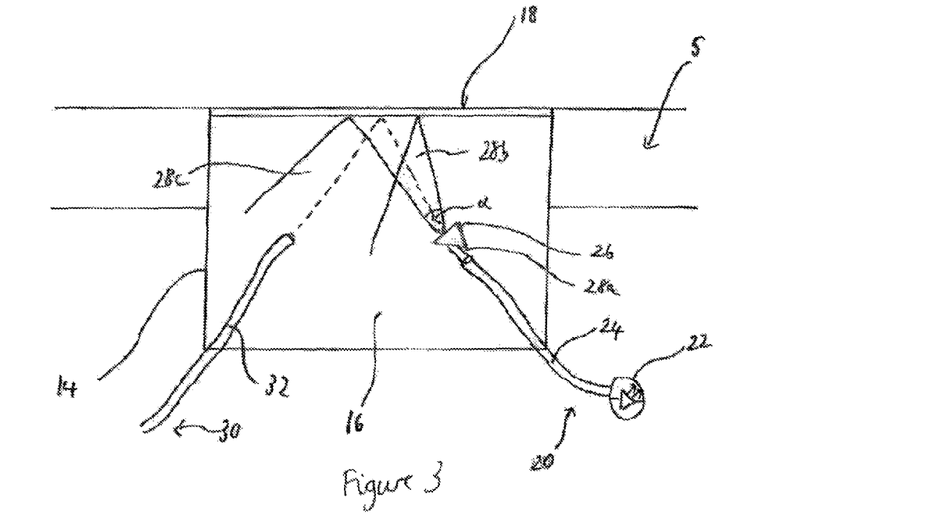
FIG. 3 illustrates an example of an optical sensor system of a wind turbine according to the first embodiment described above.

FIG. 3 illustrates one of the sensors 12 making up the sensor system 10 shown in FIG. 2, wherein the sensor is shown in situ integrated into one of the blades 5 of the wind turbine 1. Each sensor 12 comprises a sensor housing 14 defining a cavity 16 containing the sensor apparatus. One surface of the sensor housing is provided with a sensor membrane 18 which is mounted at the blade surface so that the membrane 18 separates the cavity 16 from the outside air and so that the membrane 18 is in contact with the air flow at the surface of the blade 5. The cavity is entirely sealed off from the external environment by the walls of the sensor housing 14 and the sensor membrane 18. The cavity 16 may be filled with an inert gas if desired.

The sensor membrane 18 is arranged so that it forms a smoothly continuous surface with the outer surface of the blade 5. The membrane 18 is also arranged such that it is susceptible to changes in air flow at the surface of the wind turbine blade. The thickness of the sensor membrane 18 is between 0.5 and 2 mm and the membrane is tensioned so that turbulent air flow at the blade surface will result in only small movements of the sensor membrane 18.

The sensor 12 further comprises a light source 20 aimed at the membrane 18 so that the light is incident on the inner surface of the sensor membrane at an acute angle to the surface, for example, at an angle of about 45 degrees. The light source 20 comprises a light emitting diode 22 provided outside of the sensor housing 14, connected to an optical fibre 24 which is mounted within the sensor housing 14 so that the light emitted from the exposed end of the optical fibre 24 is directed towards the sensor membrane 18. The light emitting diode 22 emits a single beam of light 28a having a range of wavelengths between around 1500 nm and 1505 nm.

A prismatic element 26 is mounted in front of the end of the optical fibre 24 such that the light beam 28a from the optical fibre 24 passes through the prismatic element 26 and is split by the prismatic element 26 to form a dispersed beam 28b with dispersion angle α in which different wavelengths of the light beam 28a are refracted by slightly different angles. As a result, each different wavelength of light is incident at a slightly different position on the inner surface of the sensor membrane 18. A dashed line indicates the part of the dispersed beam, which with highest intensity hits the light detector and the wavelength in that situation is indicative of the zero or undisplaced state of the membrane.

It will be appreciated that the illustration in FIG. 3 is schematic and is not drawn to scale. In reality, the prismatic element 26 may achieve an optical dispersion of between 50 and 100 nm per degree angle so that the dispersion angle α of the dispersed beam 28b will be significantly smaller than that illustrated schematically in FIG. 3.

The sensor 12 further comprises a light detector 30 which is positioned within the sensor housing 14 to receive light that is reflected back from the sensor membrane 18. The light detector 30 comprises an optical fibre 32 mounted such that a portion of the reflected beam is directed at the exposed end of the fibre 32. The opposite end of the optical fibre 32 is connected to a processor (not shown) remote from the sensor housing 14. The received light is transmitted down the optical fibre 32 to the processor, where the received light is split into different wavelength signals by a WDM system and the different wavelength beams are each sent to a PIN diode which detects the intensity or amplitude of the beam and outputs a signal to a differential amplifier. The processor analyses the amplitudes using a suitable mathematical processing technique and detects changes in the amplitude of the different wavelength beams which are indicative of a change in the position of the sensor membrane. The processor includes a memory which is used to store the recorded patterns of amplitude or intensity variation.

As shown in FIG. 3 and described above the light that is incident on the sensor membrane surface is in the form of a dispersed light beam 28b so that each wavelength of light is incident at the surface at a slightly different angle. Each wavelength of light is therefore also reflected away from the sensor membrane surface a slightly different angle and the reflected beam 28c will also be dispersed. The optical fibre 32 of the light detector is mounted such that is receives only a portion of the dispersed, reflective light beam corresponding to a sub-range of the overall range of wavelengths within the dispersed beam 28c. At the resting position of the sensor membrane 18, the received light is at an average wavelength $\lambda_1$.

As can be readily determined from FIG. 3, upon movement of the membrane as a result of air flow at the blade surface or vibration, the inner surface of the sensor membrane 18 moves towards or away from the light detector 30 which in turn causes a slight shift in the position of the reflected beam 28c relative to the light detector. In particular, the angle between the area sensor membrane surface on which the light beam 28b is incident and the light detector 30 is shifted. A simplified example is illustrated in FIG. 4 in which the sensor membrane moves upwards relative to the blade surface by a distance d (the position of the displaced sensor membrane is shown in dashed lines).

It can be seen that as a result of the displacement of the sensor membrane, a different portion of the dispersed, reflected beam 28c is incident on the end of the optical fibre 32 of the light detector 30. As the sensor membrane moves from its original position to the displaced position shown, the intensity of the received light at a first wavelength $\lambda_1$ corresponding to the resting position of the sensor membrane will therefore diminish whilst the intensity of the received light at a second wavelength $\lambda_2$ will increase.

The processor detects changes in the intensity of the wavelength of the received light and from this is able to calculate the distance d by which the sensor membrane has moved, as a function of time t. By recording the pattern of the displacement of the sensor membrane, it is possible to detect, e.g. when the air flow at the blade surface changes from laminar flow to turbulent flow. The processor sends a signal to a controller which is capable of controlling one or more operating parameters of the wind turbine, such as the pitch of the wind turbine blades, based on the detected turbulence. In certain cases where the turbulence indicates a build up of dirt or ice on the blade, the controller may temporarily shut down the turbine to enable the blades to be repaired or reconditioned, or to prevent further damage to the blades. A simple example of how the displacement d of the sensor membrane is related to the change in wavelength of the received light is set out below, with reference to FIG. 4.

Figure 4:
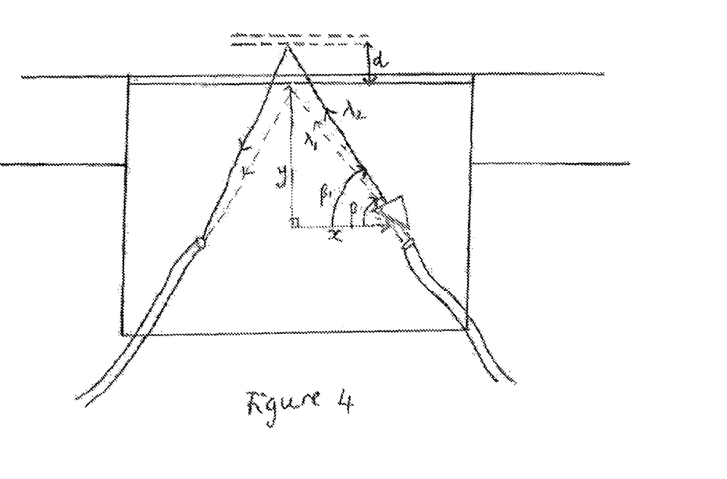
FIG. 4 provides a schematic illustration of the functioning of the optical sensor of FIG. 3 to detect movement of the sensor membrane.

In FIG. 4, only those light beams of wavelengths $\lambda_1$ and $\lambda_2$ that are received at the light detector are shown, for the sake of simplicity. For the beam of light of wavelength $\lambda_1$, shown as a dashed line, received at the light detector when the sensor membrane is in a resting position, the vertical distance y from the prismatic element 26 to the membrane 18 is equal to the horizontal distance x between the prismatic element 26 and the spot on the membrane 18 where the beam hits the surface. This means that the light of wavelength $\lambda_1$ hits the surface of the sensor membrane 18 at an angle β of 45 degrees.

When the sensor membrane moves upwards by distance d relative to the resting position, the vertical distance from the prismatic element 26 to the membrane 18 will increase to (y+d). The light beam of wavelength $\lambda_2$ that is received with high intensity at the light detector after this movement hits the surface of the sensor membrane at an angle of β' wherein:

$$\tan \beta' = \frac{y+d}{y}$$

Once the angle β' has been determined, the change in the wavelength of the light can be calculated based on the change in angle (β'-β) multiplied by the optical dispersion per angle of the beam. For example, where the membrane moves upwards by d=1 micron and y=1 mm, the change in angle (β'-β) can be calculated as 0.029 degrees. For an optical dispersion of 100 nm per degree angle, this corresponds to a change in wavelength ($\lambda_2$-$\lambda_1$) of 2.9 nm. The relationship between membrane movement and the change in detected wavelength for the particular arrangement is therefore 2.9 nm per micron of movement. A change in detected wavelength of 1 pm (picometer) therefore represents a movement of 345 pm.

By analogy, similar calculations could readily be carried out for other arrangements of the light detector and light source.

Or simply, as soon as $\lambda_1$ changes to a different wavelength, displacement of the membrane is detected. The need to quantify the displacement may serve to determine the severity of turbulence or damage to the blade, or distinguish between different states of external influence on the membrane, or just to determine whether a certain threshold has been reached.

Figure 5:
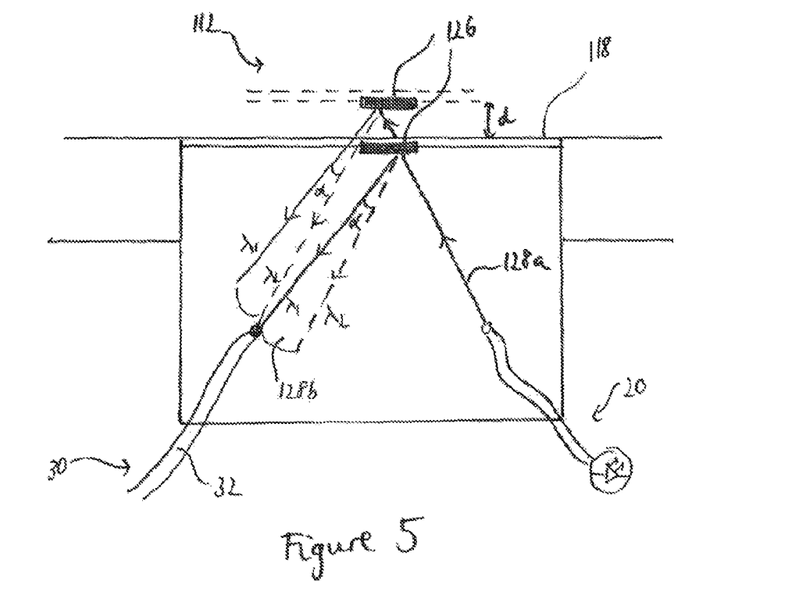
FIG. 5 illustrates an example of an optical sensor of a wind turbine according to the second embodiment described above.

FIG. 5 shows a sensor 112 having a similar arrangement to that shown in FIG. 3 and described above, except that in place of the prismatic element 26 in FIG. 3, a diffraction grating 126 is provided in a defined area at the surface of the sensor membrane 118. The light beam 128a from the light source 20 is incident on the diffraction grating 126 at the surface of the sensor membrane 118. As the light beam hits the diffraction grating 126, it will be reflected back from the grating whilst at the same time being split to form a dispersed beam 128b with dispersion angle α in which different wavelengths of the light beam are refracted by slightly different angles. As a result, each different wavelength of light is reflected back from the sensor membrane 118 in a slightly different direction towards the light detector 30.

As the sensor membrane moves towards or away from the light detector 30, the position at which the light beam 128a hits the diffraction grating 126 will shift slightly and there will be a corresponding shift in the position of the reflected, dispersed beam 128b relative to the light detector 30. Since the position of the light detector 30 is fixed, the wavelength of the light that reaches the light detector 30 will depend upon the position of the sensor membrane 118.

A simplified example is illustrated in FIG. 5 in which the sensor membrane 118 moves upwards relative to the blade surface by a distance d (the position of the displaced sensor membrane is shown in dashed lines).

It can be seen that as a result of the displacement of the sensor membrane, a different portion of the dispersed, reflected beam 128b is incident on the end of the optical fibre 32 of the light detector 30. As the sensor membrane 118 moves from its original position to the displaced position shown, the intensity of the received light at a first wavelength $\lambda_1$ (solid line) corresponding to the resting position of the sensor membrane will therefore diminish whilst the intensity of the received light at a second wavelength $\lambda_2$ (dashed line) will increase. As described above in relation to FIG. 4, this change in the wavelength of the detected light can be used to calculate the membrane movement.

Figure 6:
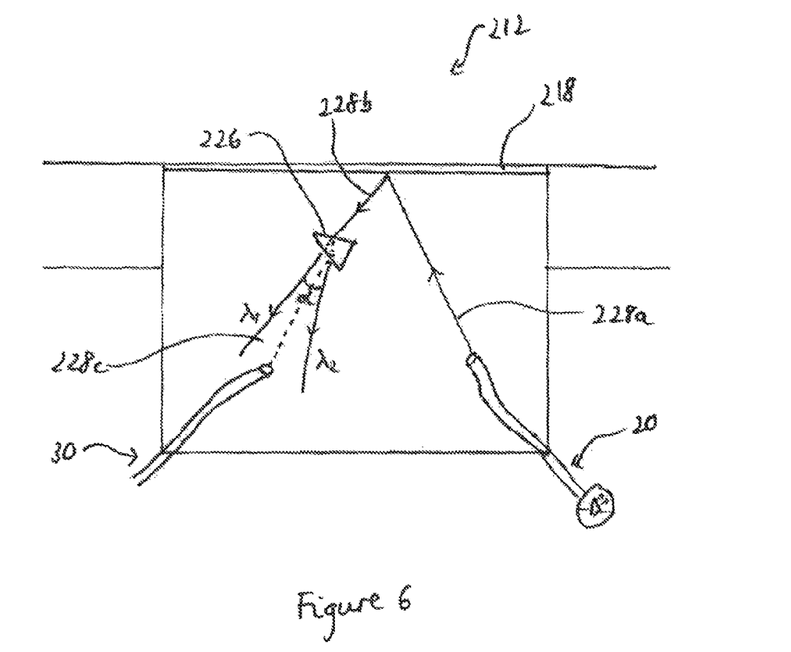
FIG. 6 illustrates an example of an optical sensor of a wind turbine according to the third embodiment described above.

FIG. 6 shows a sensor 212 having a similar arrangement to that shown in FIG. 3 and described above, except that in place of the prismatic element 26 in FIG. 3, a prismatic element 226 is provided between the sensor membrane 218 and the light detector 30. The non-dispersed light beam 228a from the light source 20 is incident on the surface of the sensor membrane 218 and reflected by the sensor membrane 218 in a non-dispersed reflected beam 228b. The reflected light beam 228b then passes through the prismatic element 226 and is split by the prismatic element 226 to form a dispersed beam 228c with dispersion angle α in which different wavelengths of the light beam 28a are refracted by slightly different angles. A dashed line indicates the part of the dispersed beam, which with highest intensity hits the light detector and the wavelength in that situation is indicative of the zero or undisplaced state of the membrane.

As the sensor membrane 218 moves towards or away from the light source 20, the position and/or angle at which the reflected light beam 228b hits the prismatic element 226 will shift slightly and there will be a corresponding shift in the angle and position of the dispersed beam 228c relative to the light detector 30. Since the position of the light detector 30 is fixed, the wavelength of the light that reaches the light detector 30 will depend upon the position of the sensor membrane 218. For example, as the sensor membrane 228 moves away from the light source 20, the intensity of the received light at a first wavelength $\lambda_1$ will increase whilst the intensity of the received light at a second wavelength $\lambda_2$ will diminish. The opposite will occur as the sensor membrane 228 moves towards the light source 20. As described above in relation to FIG. 4, this change in the wavelength of the detected light can be used to calculate the membrane movement using simple trigonometric methods.

Figure 7:
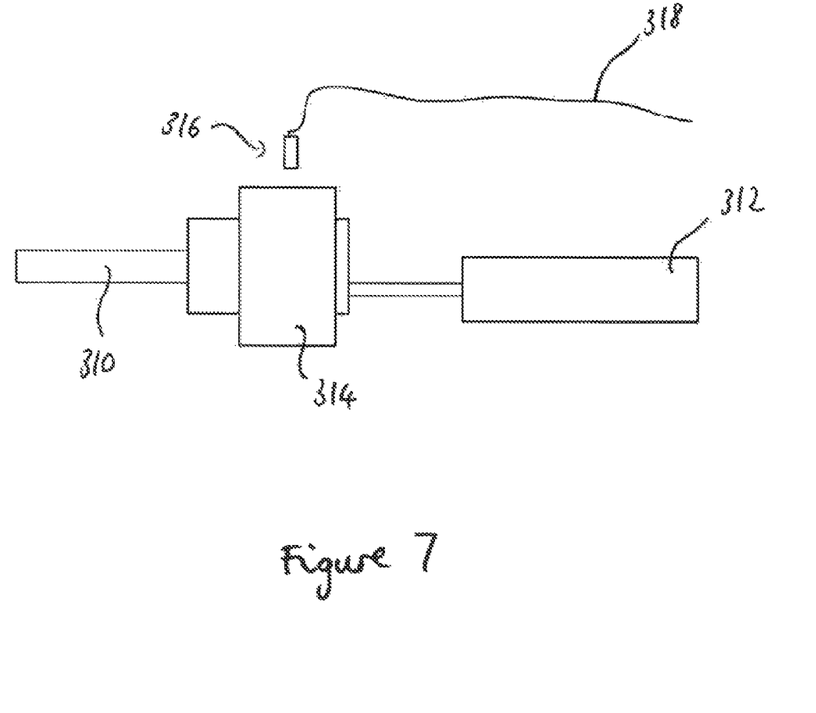
FIG. 7 illustrates the use of the optical sensor system according to the invention in the monitoring of a wind turbine generator.

FIG. 7 schematically illustrates the use of a sensor as described above in the monitoring of the sound generated by a wind turbine gear box. This arrangement is in accordance with the fourth aspect of the present invention, as described above. FIG. 7 schematically shows the components within the wind turbine nacelle, including a main shaft 310, which is coupled to a generator 312 through a gear box 314. An optical microphone 316 comprising a sensor as described above is mounted on a part of the inner nacelle casing, at a distance away from the surface of the gear box 314. The optical microphone 316 is mounted such that the sensor membrane of the sensor receives sound waves generated by the gear box 314 during operation of the turbine. As shown, the optical microphone 316 is connected to an arrangement of optical fibres 318 which provide the light source and the light detector of the sensor.

The sound waves generated by the gear box 314 during operation cause vibration of the sensor membrane of the sensor in the optical microphone. By monitoring the movement of the sensor membrane over time, using the wavelength techniques described above, it is possible to determine the frequency and amplitude of the detected sound. The frequency and amplitude of the sound are monitored over time so that any changes to the sound profile which may be indicative of damage or malfunctioning of the gear box 314 or a component thereof may be immediately identified. In the event of such damage or malfunction being identified, the wind turbine can be switched off to enable the necessary maintenance to be carried out on the gear box 314.

The invention claimed is:

1. A wind turbine including an optical sensor system comprising one or more sensors, each sensor comprising:
    a reflective sensor membrane;
    a light source for illuminating a surface of the sensor membrane with a light beam;
    an optical dispersive element arranged to disperse the light beam from the light source to produce a dispersed light beam; and
    a light detector for receiving a portion of the light beam after reflection of the light beam from the surface of the sensor membrane and after dispersion of the light beam by the optical dispersive element, wherein the wavelength of the light received at the light detector varies as a function of the displacement of the sensor membrane and wherein the light detector operatively provides an output based on changes in the wavelength of the received light,
    wherein the wind turbine further comprises a controller for receiving data from the sensor system and based on the received data controlling an operating parameter of the wind turbine.

2. A wind turbine according to claim 1 wherein the optical dispersive element is provided between the light source and the sensor membrane such that the surface of the sensor membrane is illuminated with the dispersed light beam.

3. A wind turbine according to claim 1 wherein the optical dispersive element is provided at the surface of the sensor membrane such that a dispersed light beam is reflected from the surface.

4. A wind turbine according to claim 1 wherein the optical dispersive element is provided between the sensor membrane and the light detector such that the reflected light beam is dispersed.

5. A wind turbine according to claim 1 wherein the light source emits a light beam with a wavelength range of less than 10 nm.

6. A wind turbine according to claim 5 wherein the light source emits a light beam with a wavelength range of 1500 nm to 1505 nm.

7. A wind turbine according to claim 1 wherein the optical dispersive element of the sensor is a prism or a diffraction grating for separating the wavelengths of the light in the light beam to provide the dispersed light beam.

8. A wind turbine according to claim 1 wherein the optical dispersive element of the sensor is a diffraction grating, holographic grating or angle dependent filter.

9. A wind turbine according to claim 1 wherein the light source of the sensor is a light emitting diode.

10. A wind turbine according to claim 1 wherein the light detector of the sensor comprises one or more optical fibres.

11. A wind turbine according to claim 10 wherein the light detector comprises a WDM (wavelength division multiplexing) system for splitting the received light according to wavelength.

12. A wind turbine according to claim 1 wherein the light source and the light detector of the optical sensor system are operatively provided in a sensor cavity within a wind turbine blade component and wherein the sensor membrane covers at least part of the cavity.

13. A wind turbine according to claim 1 wherein the optical sensor system comprises a plurality of optical sensors; and a processor for receiving the output from the light detectors of the plurality of optical sensors and determining from the output the displacement of the sensor membrane dependent on the intensity and wavelength of light received at a light detector.

14. A wind turbine according to claim 13 wherein the optical sensor system further comprises a memory for recording the outputs from the light detectors of the plurality of optical sensors over a predetermined time period wherein the processor analyses the recorded outputs in order to determine a condition of the wind turbine over the time period.

15. A wind turbine according to claim 13 further comprising a controller for receiving data from the processor and based on the received data controlling an aerodynamic parameter of the wind turbine.

16. A wind turbine according to claim 13 wherein the optical sensor system is adapted for operatively monitoring the airflow at a surface of a wind turbine component, wherein the sensor membrane is operatively mounted at a surface of a wind turbine component for monitoring air flow across the surface, wherein the processor determines from the output of the light detectors the type of airflow across the sensor membrane.

17. A wind turbine according to claim 16 wherein the optical sensor system is adapted for operatively detecting turbulent air flow at the surface of the wind turbine component, wherein the processor analyses variations in the wavelength of the received light at the light detectors over a predetermined period of time to determine whether the air flow over the sensor membrane is turbulent.

18. A wind turbine according to claim 17 wherein the optical sensor system forms part of a blade control system and wherein the controller operatively receives data from the processor of the sensor system and, based on the detection of turbulent air flow, controls an aerodynamic parameter of the blade.

19. A wind turbine according to claim 1 wherein the optical sensor system is mounted at the surface of a wind turbine component and is adapted for operatively detecting vibration of the wind turbine component.

20. A wind turbine according to claim 1 wherein the optical sensor system is adapted to provide an optical microphone for operatively monitoring the sound generated by a wind turbine component such that the optical microphone is tuned to detect sound waves within a defined range of frequency, wherein the defined range of frequency varies according to the type of wind turbine component to be monitored.

21. A wind turbine according to claim 1 wherein the optical sensor system is operatively mounted on a wind turbine blade such that the sensor membrane is integral to the surface of the blade.

22. An optical sensor system for a wind turbine, the sensor system having one or more optical sensors, each sensor comprising:
a reflective sensor membrane;
a light source for illuminating a surface of the sensor membrane;
an optical dispersive element arranged to disperse the light beam from the light source to produce a dispersed light beam; and
a light detector for receiving a portion of the light beam after reflection of the light beam from the surface of the sensor membrane and after dispersion of the light beam by the optical dispersive element, wherein the wavelength of the light received at the light detector varies as a function of the displacement of the sensor membrane and wherein the light detector operatively provides an output based on changes in the wavelength of the received light.

23. A method, comprising:
receiving, at a controller, a data signal from an optical sensor system comprising one or more sensors, each sensor comprising:
an optical dispersive element arranged to disperse a light beam from a light source to produce a dispersed light beam; and
a light detector for receiving a portion of the light beam after reflection of the light beam from a surface of a sensor membrane and after dispersion of the light beam by the optical dispersive element, wherein the wavelength of the light received at the light detector varies as a function of the displacement of the sensor membrane and wherein the light detector operatively provides an output based on changes in the wavelength of the received light; and
issuing, from the controller to the wind turbine, a control signal configured to control an operating parameter of the wind turbine, the control signal being based on the received data signal.

* * * * *